United States Patent [19]

Wattley et al.

[11] Patent Number: 4,820,818

[45] Date of Patent: Apr. 11, 1989

[54] PROCESS FOR THE GEOMETRIC STEREOSELECTIVE DEHYDRATION OF 3-(9-CHLORO-5,6-DIHYDRO-11H-11-HYDROXY-PYRROLO-(2,1-B)(3)-BENZAZEPIN-11-YL)-N,N-DIMETHYL-1-PROPANAMINE

[75] Inventors: Ruth V. Wattley, Edison; Gerard R. Kieczykowski, Westfield, both of N.J.

[73] Assignee: Merck & Co., Inc., Rahway, N.J.

[21] Appl. No.: 189,009

[22] Filed: May 2, 1988

[51] Int. Cl.[4] ............................................. C07D 487/04
[52] U.S. Cl. .................................... 540/586; 514/906;
   548/530; 548/532; 548/533; 548/534

[58] Field of Search .................. 514/411, 906; 564/88,
   564/379; 568/319; 540/586; 548/530, 532, 533, 534

[56] References Cited

U.S. PATENT DOCUMENTS 4,112,112  9/1978  Rooney et al. ...................... 514/411

Primary Examiner—Donald G. Daus
Assistant Examiner—Miriam Sohn
Attorney, Agent, or Firm—William H. Nicholson; Michael C. Sudol, Jr.

[57] ABSTRACT

The muscle relaxant (E)-3-(9-chloro-5,6-dihydro-11H-pyrrolo[2,1-b][3]benzazepin-11-ylidene-N,N-dimethyl-1-propanamine is prepared by the geometric stereoselective dehydration of the intermediate carbinol with acidic agents and organic bases and low temperatures.

3 Claims, No Drawings

PROCESS FOR THE GEOMETRIC STEREOSELECTIVE DEHYDRATION OF 3-(9-CHLORO-5,6-DIHYDRO-11H-11-HYDROXY-PYRROLO-(2,1-B)(3)-BENZAZEPIN-11-YL)-N,N-DIMETHYL-1-PROPANAMINE

SUMMARY OF THE INVENTION

This invention is concerned with a novel process for the preparation of the muscle relaxant compound of structural formula:

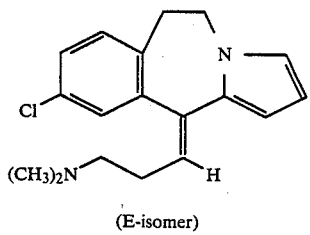

(E-isomer)

The process comprises dehydration of the intermediate carbinol of structural formula

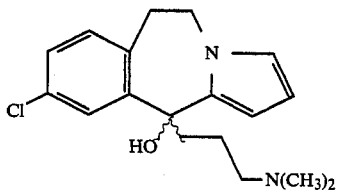

by treating it with an acidic agent at low temperatures whereby the product, potentially an (E, Z)-mixture of geometric isomers, is greatly enriched with respect to the desired (E)-isomer.

BACKGROUND OF THE INVENTION

The compound, which is the product of the novel process of this invention is a skeletal muscle relaxant useful in the treatment of muscle spasms and other similar muscle disorders associated with or caused by injury, disease, or arising spontaneously of unknown etiology. The compound and its utility are disclosed in U.S. Pat. No. 4,112,112, the disclosure of which is incorporated herein by reference. The process in U.S. Pat. No. 4,112,112 for preparing the compound of interest also comprises the dehydration of the same intermediate carbinol as utilized in the present invention. However, the dehydration in the prior art process is conducted at 0° to 100° C. which results in a mixture of the E and Z isomers. These isomers are separable by chromatography on an adsorbent such as silica gel and elution with a suitable solvent. From a commercial standpoint this is a very expensive, labor intensive unsatisfactory operation.

Now with the present invention there is provided a novel process wherein the dehydration is conducted at about −90° C. to −50° C. whereby the ratio of the E:Z-isomers is greater than about 95:5 from which the substantially pure E-isomer is readily available without the need for chromatographic purification, as in the prior art processes.

DETAILED DESCRIPTION OF THE INVENTION

The process of this invention comprises an improvement in the prior art process for the preparation of the compound of structural formula

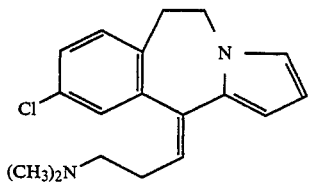

which comprises dehydration of the compound of structural formula:

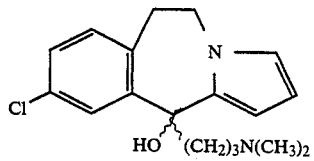

by treatment with an acid or acid precursor such as hydrochloric acid, oxalic acid, trifluoroacetic acid, formic acid, acetic acid, trifluoroacetic anhydride, trichloroacetic acid, or phosphorousoxychloride and a tertiary amine in a halocarbon, such as chloroform, or methylene chloride, for about 5 minutes to 24 hours at about 0° to 100° C., wherein the improvement comprises conducting the dehydration at about −90° to −50° C., preferably about −80° to −60° C. whereby the ratio of E to Z isomers in the product is about 95 to 5.

In addition to the reagents mentioned previously, strong bases such as butyllithium, grignards, lithium diisopropylamide (LDA), sodium hydride and lithium and sodium hexamethyldisilazide can be used in tetrahydrofuran, diethyl ether, 1,2-dimethoxyethane, dioxane, toluene, or cyclohexane with acidic reagents such as trifluoroacetic anhydride, acetic anhydride or methanesulfonyl chloride.

Amine bases such as trimethylamine, triethylamine, tributylamine, diisopropylethylamine, dimethylethylamine, diisopropylamine, or hexamethyldisilazane can be used with reagents such as methanesulfonyl chloride, ethanesulfonyl chloride, thionyl chloride, diethyl chlorophosphate, chlorodiphenylphosphine, acetic anhydride, trifluoroacetic anhydride (TFAA), acetyl chloride, chloroacetyl chloride, trichloroacetyl chloride, trichloroacetic-formic anhydride or acetic-formic anhydride in solvents such as diethyl ether, 1,2-dimethoxyethane, dioxane, cyclohexane, methylene chloride, 1,2-dichloroethane or carbon tetrachloride.

EXAMPLE 1

Preparation of 3-(4-chloro-5,6-dihydro-11H-pyrrolo[2,1-b][3]benzazepin-11-ylidene)-N,N-dimethyl-1-propanamine (mixture of E and Z isomers)

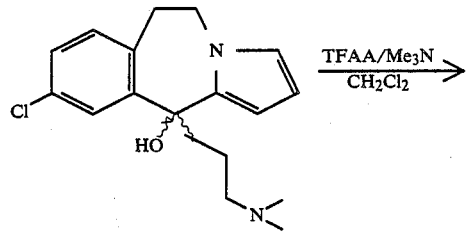

1

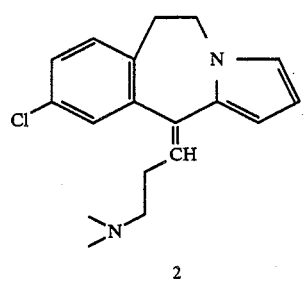

2

| | |
|---|---|
| $C_{18}H_{23}ClN_2O$ | $C_{18}H_{21}ClN_2$ |
| MW 318.8 | MW 300.8 |

| | |
|---|---|
| Carbinol (1) | 57 g (0.179 moles) |
| Methylene chloride | 500 ml |
| Trimethylamine | 27 g (3.35 equiv.) |
| Trifluoroacetic anhydride (TFAA) | 25 ml (0.99 equiv.) |
| Sodium hydroxide (2.5 N) | 200 ml |
| Hexanes | 420 ml |
| Calgon ADP Charcoal | 3 g |

The carbinol and the methylene chloride are charged to a 1 l nitrogen blanketed flask fitted with a mechanical stirrer and a thermocouple. The solution is cooled to −50° C. and the trimethylamine charged subsurface while the solution is cooled further. The solution is cooled to −75° to −80° C. and the TFAA is charged dropwise so as to maintain a reaction temperature < −70° C.

The reaction is quite exothermic and takes 80 minutes for the addition. Temperature is critical to maintain a desirable E:Z ratio.

The reaction is held at −70°/−78° C. for 1 hour.

At this point if the HPLC indicates starting carbinol, additional TFAA is added dropwise.

The reaction is allowed to warm to −50° C. over a one hour period once the addition is complete. The reaction is then quenched by the addition of the sodium hydroxide and the two phase system is warmed to 20° C.

The reaction can be warmed first then quenched.

The layers are separated and the aqueous layer is extracted with 50 ml of methylene chloride. The combined organic solution is concentrated to an oil and hexanes (400 ml) are added. The mixture is heated to 50° C. and 3 g of activated carbon is added. After aging for 30 minutes at 50° C. the suspension is filtered through a pad of filter aid. The amber solution is concentrated to a thick slurry (ca. 150 ml in volume), cooled to 0° C., aged 1.5 hours and filtered. The filter cake is washed with 20 ml of hexanes and the product dried in vacuo protected from light.

Yield 45.5 g (85%), pale yellow crystals (99.3% E isomer, 0.3% Z isomer, 0.4% other).

HPLC:
1% ET₃N/EtOAc-silica
RT E isomer=3.3 min
RT Z isomer=3.9 min
RT Carbinol=4.7 min
RT Trifluoroacylated=1.8, 2.2 min Employing the procedure substantially as described in the foregoing Example but employing the reagents and conditions indicated in the Table, there are realized the E:Z isomer ratios also indicated in the Table.

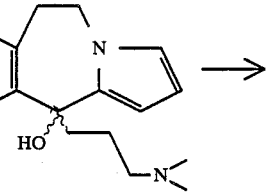

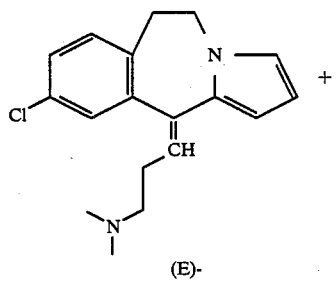

(E)-

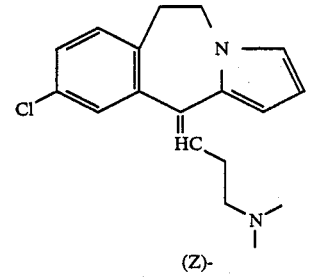

(Z)-

| Reagents | Solvent | Temp. | Ratio E:Z | Chem. Yield |
|---|---|---|---|---|
| SOCl₂/Pyr | CH₂Cl₂ | 0 | 30/70 | — |
| SOCl₂/Et₃N | CH₂Cl₂ | 0 | 37/63 | — |
| SOCl₂/Et₃N | CH₂Cl₂ | −78 | 65/35 | — |
| MeSO₂Cl/Pyr | CH₂Cl₂ | 0 | N.R. | — |
| MSCl/Et₃N | CH₂Cl₂ | 0 | 65/35 | — |
| MSCl/Et₃N | Et₂O | 0 | 65/35 | — |
| MSCl/Et₃N | EDC | 0 | 60/40 | — |
| MSCl/Et₃N | CH₂Cl₂ | −20 | 87/12 | 81 |
| MSCl/Et₃N | Et₂O | −15 | 73/27 | — |
| MSCl/Bu₃N | Et₂O | −15 | 61/29 | — |
| MSCl/LDA | Et₂O | −10 | 78/22 | — |
| MSCl/BuLi | Et₂O | −10 | 62/26 | — |
| TFAA/ET₃N | CH₂Cl₂ | −20 | 87/11 | 81 |
| TFAA/ET₃N | CH₂Cl₂ | −40 | 92/4 | 95 |
| TFAA/ET₃N | CH₂Cl₂ | −60 | 98/2 | 96 |
| TFAA/ET₃N | CH₂Cl₂ | −78 to −60 | 99/1 | — |
| TFAA/Me₃N | CH₂Cl₂ | −78 to −60 | 98/2 | — |

What is claimed is:

1. In a process for the preparation of the compound of structural formula:

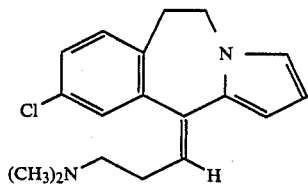

which comprises the treatment of a compound of structural formula:

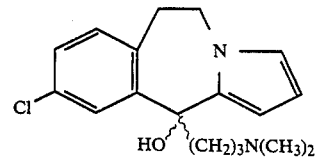

with an acid or acid precursor in the presence of a tertiary amine in a halocarbon solvent at about 0° to 100° C., wherein the improvement comprises conducting the reaction at −90° to −50° C.

2. The improved process of claim 1, wherein the reaction is conducted at −80° to −60° C.

3. The process of claim 2 wherein the acid precursor is trifluoroacetic anhydride, the tertiary amine is trimethylamine and the halocarbon solvent is methylene chloride.

* * * * *